United States Patent [19]

Shaar et al.

[11] Patent Number: 4,885,163

[45] Date of Patent: Dec. 5, 1989

[54] TOPICAL USE OF IGF-II FOR WOUND HEALING

[75] Inventors: Carl J. Shaar; Michele C. Smith, both of Indianapolis, Ind.

[73] Assignee: Eli Lilly and Company, Indianapolis, Ind.

[21] Appl. No.: 18,251

[22] Filed: Feb. 24, 1987

[51] Int. Cl.$^4$ ............ A61K 39/00; A61K 45/02
[52] U.S. Cl. ............................ 514/2; 435/85; 530/303; 530/399
[58] Field of Search ............ 435/85; 424/110; 530/303

[56] References Cited

U.S. PATENT DOCUMENTS 4,014,861  3/1977  Geiger ............ 530/303
4,444,683  4/1984  Kim ............ 530/303

OTHER PUBLICATIONS

Thornton, J. W., Hess, C. A., Cassingham, V., and Bartlett, R. H. *Burns* 8, 156–160 (1982).
Niall, M., Ryan, G. B., and O'Brien, B. M., *J. Surg. Res.* 33, 164–169 (1982).
Brown, G. L., Schultz, G., Brightwell, J. R., and Tobin, G. R., *J. Exp. Med.* 163, 1319–1324 (1986).
Buckley, A., Davidson, J. M., Kamerath, C. D., Wolt, T. B., and Woodward, S. C., *Proc. Natl. Acd. Sci. USA* 82, 7340–7344 (1985).
Lawrence, W. T., Grotendorst, G. R., and Norton, J. A., *Surg. Forum* 36, 575–577 (1985).
Spoon, M. B., Roberts, A. B., Shull, J. H., and Smith, J. M., Ward, J. M., and Sodek, J., *Science* 219, 1329–1331 (1983).
Schultz, G. S., White, M., Mitchell, R., Brown, G., Lynch, J., Twardzik, D. R., and Todaro, G. J., *Science* 235, 350–352 (1987).
Leitzel, K., Cano, C., Marks, J., and Lipton, A., *J. Neuroscience Res.* 8, 413–417 (1982).
Leitzel, K., Cano, C., Marks, J., and Lipton, A., *Clinical Research* 31, 582A (1983).
Froesch, E. R., and Zapf, J., *Diabetologia* 28, 485–493 (1985).
Froesch, E. R., Schmid, Chr., Schwander, J., and Zapf, J., *Ann. Rev. Physiol.* 47, 443–467 (1985).
Bhaumick, B., and Bala, R. M., *Endocrine Society Abstract* 552, Jun., 1986
Skover, G. R., and Michaeli, *Federation Proceedings* 43, (4), 992 (1984).

*Primary Examiner*—Peter D. Rosenberg
*Attorney, Agent, or Firm*—William C. Martens; Leroy Whitaker

[57] ABSTRACT

There is herein described an invention for promoting the rate and improving the quality of wound healing by topically applying insulin-like growth factor-II to the wound.

14 Claims, No Drawings

TOPICAL USE OF IGF-II FOR WOUND HEALING

BACKGROUND OF THE INVENTION

It for some time has been recognized that a number of trophic factors, due to their stimulation of cell growth and differentiation, may have an enhancement on wound healing.

Several studies measuring the efficacy of epidermal growth fact (EGF) in wound healing have been undertaken with mixed results. Thornton et al., *Burns* 8, 156-160 (1982) applied EGF topically to scald burns in rats. Only an insignificant healing advantage over control was seen.

Niall et al., *J. Surg. Res.* 33, 164-169 (1982) reported an enhancing effect on wound healing in mice upon topical administration of EGF.

Brown et al., *J. Exp. Med.* 163, 1319-1324 (1986), studied the activity of EGF topically applied to wounds in miniature pigs. They report that it increased the rate of epithelialization of split-thickness wounds in vivo.

A fourth paper, Buckley et al., *Proc. Natl. Acad. Sci USA* 82, 7340-7344 (1985), studied the effects of EGF upon slow release from subcutaneously-implanted sponges in rats. They conclude that local sustained presence of EGF accelerates the process of wound healing.

Studies by Lawrence et al., *Surg. Forum* 36, 575-577 (1985), and Sporn et al., *Science* 219, 1329-1331 (1983) both suggest an acceleration of wound healing in rats upon administration of transforming growth factor (TGF), and in Lawrence et al., a further enhancement upon the combined use of TGF, EGF, and platelet-derived growth factor (PDGF).

Shultz et al., *Science* 235, 350-352 (1987), reported that topically applied transforming growth factor-alpha (TGF-α) and vaccinia growth factor (VGF) in antibiotic cream accelerated epidermal regeneration in partial thickness dermal burns (second degree) on the backs of pigs.

Leitzel et al., *J. Neuroscience Research* 8, 413-417 (1982) studied nerve growth factor and found that it was ineffective when applied topically to full-thickness skin wounds in the Syrian hamster.

Leitzel et al., *Clinical Research* 31, 582A (1983), investigated the effect of a number of topically applied mitogenic preparations, viz., dexamethasone and insulin, PDGF, fibroblast growth factor (FGF), thrombin, Defined medium F for Fibroblasts, liver cell supernatant, EGF, NGF, and colostrum, to wounds in Syrian hamsters. They conclude that none of these agents has any effect on accelerating the healing of skin wounds.

Recently, interest has been generated in the IGFs, insulin-like growth factor-I (IGF-I), also termed Somatomedin C, and insulin-like growth factor-II (IGF-II). Froesch et al., *Diabetologia* 28, 485-493 (1985), reports (page 490) that "the major effects of IGFs are on growth of cells of mesodermal origin and on differentiation." They further report that the "constant high levels of IGF in the bound form in serum may, therefore, serve several functions: replacement of dying cells, repair mechanisms, matrix synthesis and perhaps also a constant stabilization of cells keeping them from transforming and dedifferentiating."

Froesch et al., *Ann. Rev. Physiol.* 47, 443-467 (1985) state (page 448), "IGF-II has one-third the potency of IGF-I in stimulating DNA synthesis in human fibroblasts and one-fifth the potency in rat osteoblasts. It is possible that these IGF-II concentrations are sufficient to sustain tissue repair and regenerative processes."

Bhaumick et al., *Endocrine Society Abstract* 552, June, 1986, report, in studies using a mouse limb bud organ culture, findings that suggest that IGF-II may have a predominant role in undifferentiated cell proliferation whereas IGF-I stimulates differentiation and then proliferation.

Skover et al., *Federation Proceedings* 43 (4), 992 (1984), in studies using somatomedin-C (IGF-I), suggest that it is a specific stimulus for collagen synthesis in human fibroblasts and, thus, may be an important regulator of wound repair and may have possible applications in the modulation of healing.

In the context of the foregoing, we have discovered that the healing of wounds can be greatly enhanced by topical administration of IGF-II. This is quite unexpected, especially since we have further discovered that IGF-I topically has at best minimal enhancing effect on wound healing.

SUMMARY OF THE INVENTION

Thus, this invention is directed to a pharmaceutical formulation comprising insulin-like growth factor-II and a pharmaceutically acceptable carrier suitable for topical administration.

In addition, this invention is directed to a method for promoting the rate and improving the quality of wound healing, which comprises topically applying to such wound insulin-like growth factor-II in an amount sufficient to reduce the normal healing time.

DETAILED DESCRIPTION OF THE INVENTION

As indicated above, the present invention is directed to topical formulations containing IGF-II and to a method for enhancing wound healing by topically applying IGF-II to such wound.

IGF-II is a protein containing 67 amino acid residues and has the following sequence:

$$
\begin{aligned}
&\phantom{H-Ala-Tyr-Arg-Pro-}5\\
&H-Ala-Tyr-Arg-Pro-Ser-Glu-Thr-Leu-Cys-\\
&\phantom{-}10\phantom{-Gly-Glu-Leu-}15\\
&-Gly-Gly-Glu-Leu-Val-Asp-Thr-Leu-Gln-\\
&\phantom{-}20\phantom{-Cys-Gly-Asp-}25\\
&-Phe-Val-Cys-Gly-Asp-Arg-Gly-Phe-Tyr-Phe-\\
&\phantom{-}30\phantom{-Pro-Ala-Ser-}35\\
&-Ser-Arg-Pro-Ala-Ser-Arg-Val-Ser-Arg-Arg-\\
&\phantom{-}40\phantom{-Gly-Ile-Val-}45\\
&-Ser-Arg-Gly-Ile-Val-Glu-Glu-Cys-Cys-\\
&\phantom{-}50\phantom{-Ser-Cys-Asp-}55\\
&-Phe-Arg-Ser-Cys-Asp-Leu-Ala-Leu-Leu-\\
&\phantom{-------------}60\\
&-Glu-Thr-Tyr-Cys-Ala-Thr-Pro-Ala-\\
&\phantom{---------------}65\\
&\phantom{--------------}-Lys-Ser-Glu-OH
\end{aligned}
$$

The molecule contains disulfide bonds resulting from bridged cysteine residues as follows:

| |
|---|
| Cys 9–Cys 47 |
| Cys 21–Cys 60 |
| Cys 46–Cys 51 |

IGF-II can be produced by routine recombinant DNA methodology, procedures for which are described in a number of patent publications, e.g., European patent application No. 176,341; European Patent Application No. 128,733; European patent application No. 123,228; and PCT patent application No. W085/00831.

In addition to having a rate-promoting effect on wound healing, it has been discovered that topical administration of IGF-II has the accompanying effect of improving the quality of wound healing. Thus, topical use of IGF-II (1) increases collagen turnover (more new collagen is formed with accompanying added removal of old collagen), (2) increases fibroblast infiltration, (3) provides more complete epithelialization of the wounds, and (4) improves the cleanliness of the wound (increased phagocytosis of foreign objects within the wound).

Moreover, although it is recognized that IGF-II exhibits insulin-like activity, topical administration of IGF-II at doses sufficient to accelerate wound healing does not influence serum glucose levels, i.e., lacks systemic insulin-like activity.

IGF-II is effective in treating any of a wide range of wounds. Examples of the types of wounds treatable using IGF-II are chemical or thermal burns; skin graft donor and transplant sites; cutaneous ulcers, including but not limited to decubitus ulcers, diabetic ulcers, vascular stasis ulcers, and necrobiosis lipoidicum ulcers; surgical wounds, wound dehiscence, including but not limited to the abdominal, thigh, and chest areas; corneal trauma and transplants; tooth extractions and oral surgery; disruption of a mucous membrane, including but not limited to the gastrointestinal tract (ulcerative colitis) and bladder; and any of a wide range of other traumatic interruptions of connective tissue, e.g., abrasions.

The formulations of this invention are designed for topical administration. Typical of such formulations are ointments, creams, and gels. A preferred formulation for use in accordance with this invention is an ointment.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient (IGF-II) is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (IGF-II) customarily is added in an amount to achieve the desired concentration.

Gels comprise a base selected from an oleaginous base, water, or an emulsion-suspension base, such as aforedescribed. To the base is added a gelling agent which forms a matrix in the base, increasing its viscosity. Examples of gelling agents are hydroxypropyl cellulose, acrylic acid polymers, and the like. Customarily, the active ingredient (IGF-II) is added to the formulation at the desired concentration at a point preceding addition of the gelling agent.

The amount of IGF-II incorporated into the formulation of this invention is not critical; the concentration should only be in a range sufficient to permit ready application of the formulation to the wound area in an amount which will deliver the desired amount of IGF-II.

The customary amount of formulation to be applied to a wound will depend upon wound size and concentration of IGF-II in the formulation. Generally, the formulation will be applied to the wound in an amount affording from about 1 to about 500 $\mu$g IGF-II per $cm^2$ of wound. Preferably, the applied amount of IGF-II will range from about 30 to about 300 $\mu$g/$cm^2$, more preferably, from about 50 to about 200 $\mu$g/$cm^2$, and, most preferably, from about 60 to about 100 $\mu$g/$cm^2$.

The following examples are provided to illustrate the present invention. They are not intended to be limiting upon the scope thereof.

EXAMPLE 1

Culture of *Escherichia coli* RV308/pCZ20 and Isolation of Plasmid pCZ20

A. Culture of *Escherichia coli* RV308/pCZ20

One hundred ml of TY broth (10 g tryptone, 5 g yeast extract and 5 g NaCl per liter) containing 50 $\mu$g/ml kanamycin sulfate were inoculated with a culture of *E. coli* RV308/pCZ20 (deposited at the Northern Regional Research Center under Accession No. NRRL B-15881)and incubated with shaking for ~16 hours at 20°–25° C. The 100 ml of culture were then transferred to a flask containing 900 ml TY broth supplemented with 50 $\mu$g/ml kanamycin. The diluted culture was then incubated with shaking at 37° C. for 2–3 hours. The 37° C. temperature of incubation induced high plasmid copy number.

B. Isolation of Plasmid pCZ20

The cells were pelleted by centrifugation (4° C. at 10,000 rpm for 5 minutes), and the pellet was resuspended in 20 ml of a solution containing 25 mM Tris-HCl, pH 8; 10 mM ethylenediamine tetraacetic acid (EDTA); and 50 mM glucose and supplemented with 2 mg/ml lysozyme. The resuspended cells were incubated on ice for 15 minutes, and then 40 ml of a solution containing 1% sodium dodecyl sulfate (SDS) and 0.2N NaOH were added, and the mixture was stirred. After the cells were completely lysed, 30 ml of cold 3M NaOAc, pH 4.8, were added, and the resulting solution was mixed and incubated on ice for one hour. The solution was then centrifuged at 20,000 rpm for 30 minutes. After centrifugation, the pellet was discarded and 3 volumes of cold, absolute ethanol were added to the supernatant. The resulting mixture was chilled at −70° C. for 10–20 minutes and then was centrifuged at 10,000 rpm for 10 minutes to pellet the DNA.

The DNA pellet was resuspended in 10 ml of TE buffer (10 mM Tris-HCl, pH 7.5 and 1 mM EDTA), and then 0.1 ml of a 5 mg/ml RNAse A solution and 10 $\mu$l of a 2500 U/ml RNAse T solution were added. The resulting solution was incubated at 65° C. for 20 minutes after which 30 g of CsCl were added. The volume was adjusted to 38 ml by addition of TE buffer. Two ml of ethidium bromide were added, and ultracentrifugation at 49,000 rpm for 17 hours in a vertical rotor was performed to band the plasmid DNA.

After the plasmid band was removed from the centrifugation tube, the ethidium bromide was extracted with isopropyl alcohol (saturated with CsCl and $H_2O$), and the CsCl was removed by dialysis against TE buffer. The resultant plasmid pCZ20 DNA was suspended in TE buffer at a concentration of 1 µg/ml, and the mixture was stored at −20° C.

EXAMPLE 2

Isolation of the ~0.43 kb EcoRI Restriction Fragment Encoding trpLE1 From Plasmid pCZ20

About 30 µl (30 µg) of the plasmid pCZ20 DNA, isolated above, were added to 10 µl 10X EcoRI buffer (1.5M Tris-HCl, pH 7.2; 500 mM NaCl; and 10 mM dithiothreitol), 2 µl EcoRI restriction enzyme (~60 units) and 58 µl H$_2$O. After mixing, the reaction mixture was placed in a 37° C. water bath for one hour, and the solution then was electrophoresed on a 1% agarose gel until the desired ~0.43 kb EcoRI fragment was clearly separated from the other digestion products. Visualization of the electrophoresed DNA was accomplished by staining the gel in a dilute solution of ethidium bromide (0.5 µg/ml) and exposing the stained gel to long-wave UV light. After locating the desired fragment, a small slit was made in the gel and a small piece of Schleicher and Schuell (Keene, NH 03431) NA-45 DEAE membrane was placed in the slit. Upon further electrophoresis the DNA non-covalently bound to the DEAE membrane. After the desired fragment was bound to the DEAE membrane, the membrane was removed and rinsed with low salt buffer (150 mM NaCl; 0.1 mM EDTA; and 20 mM Tris-HCl, pH 8). The membrane then was placed in a small tube and immersed in high salt buffer (1M NaCl; 0.1 mM EDTA; and 20 mM Tris HCl, pH 8) and incubated at 65° C. for one hour to remove the DNA from the DEAE paper. After incubation, the incubation buffer was collected and the membrane rinsed with high salt buffer. The rinse solution was pooled with the incubation buffer before collecting the desired DNA fragment.

The volume of the high salt-DNA solution was adjusted to an NaCl concentration of 0.25M, and three volumes of cold, absolute ethanol were added. The resulting solution was mixed and maintained at −70° C. for 10–20 minutes. After chilling, the solution was centrifuged at 15,000 rpm for 15 minutes. After another precipitation to remove residual salt, the DNA pellet was rinsed with ethanol, dried, resuspended in 20 µl of TE buffer and constituted ~0.25 µg of the desired trpLE1-encoding EcoRI restriction fragment.

EXAMPLE 3

Construction of IGFII-Encoding DNA

The synthesis of the coding region of the IGFII gene was accomplished by the following generalized procedure: (A) 38 single-stranded deoxyribooligonucleotides, each containing between 9 and 15 deoxyribonucleotides, were synthesized by the improved phosphotriester method; (B) some of the 38 single-stranded DNA molecules were phosphorylated; and (C) a series of annealing and ligating reactions were carried out to form two double-stranded DNA molecules, each comprising about half of the coding region of the gene.

The two fragments formed above were ultimately inserted into plasmid pBR322 to construct the entire IGFII coding sequence on a single DNA molecule. A more detailed description of steps A–C is now provided.

A. Synthesis of Single-Stranded DNA Fragments

The 38 deoxyribooligonucleotides listed in Table 1 below were synthesized by the improved phosphotriester method of Hsiung et al., 1983, *Nucleic Acids Research*, 11:3227. A variety of well-known DNA-synthesizing instruments suitable for synthesizing the single-stranded fragments are also available.

TABLE 1

| # | Sequence | Size |
|---|----------|------|
| 1 | AATTCATGGCT | 11 mer |
| 2 | TATCGACCGTCT | 12 mer |
| 3 | GGCGGCGAACTG | 12 mer |
| 4 | AAGCCACGGT | 10 mer |
| 5 | GTTGACACTCTG | 12 mer |
| 6 | CGCCGCAAACGA | 12 mer |
| 7 | GCTTCTACTTC | 11 mer |
| 8 | TCTCGTCCGG | 10 mer |
| 9 | CTTCTCGTGTTT | 12 mer |
| 10 | CTAGACGTTC | 10 mer |
| 11 | TCGTGGCAT | 9 mer |
| 12 | CGTTGAAGAATG | 12 mer |
| 13 | TCTTGCGACCTG | 12 mer |
| 14 | CAGTTCGTTTGC | 12 mer |
| 15 | GCTCTGCTGG | 10 mer |
| 16 | AAACTTACTGC | 11 mer |
| 17 | GCTACTCCTGCT | 12 mer |
| 18 | AAATCTGAATAATAG | 15 mer |
| 19 | CGATAAGCCATG | 12 mer |
| 20 | GTTTCAGACGGT | 12 mer |
| 21 | CAACCAGTTCGC | 12 mer |
| 22 | ACTGCAGAGTGT | 12 mer |
| 23 | CTGCTTCCGC | 10 mer |
| 24 | GGCGACCGTG | 10 mer |
| 25 | GAGAGAAGTAG | 11 mer |
| 26 | GAAGCCGGAC | 10 mer |
| 27 | CTAGAAACACGA | 12 mer |
| 28 | ACGAGAACGT | 10 mer |
| 29 | AACGATGCC | 9 mer |
| 30 | AAGCAGCATTCTTC | 14 mer |
| 31 | TCGCAAGAGCGG | 12 mer |
| 32 | CAGAGCCAGG | 10 mer |
| 33 | AAGTTTCCAG | 10 mer |
| 34 | AGTAGCGCAGT | 11 mer |
| 35 | AGATTTAGCAGG | 12 mer |
| 36 | GATCCTATTATTC | 13 mer |
| 37 | GAAACTCTGTGC | 12 mer |
| 38 | CGCCGCACAGA | 11 mer |

B. Phosphorylation

After purifying each oligonucleotide by thin layer chromatography and reverse phase high pressure liquid chromatography, certain of the 38 single-stranded DNA fragments of Table 1 were phosphorylated according to the teaching of Hsiung et al., 1983, supra, in order to facilitate the ligation and construction of the IGFII gene-encoding DNA fragments. Some of the fragments are depicted as having "$^{32}$P" at their 5' end, since tracer amounts of γ-$^{32}$P-ATP were used in the phosphorylation reactions.

C. Annealing and Ligation

Fragments 1, 2, 3, 19, 20, 21, 37 and 38 were annealed and ligated to form Duplex I:

```
5' HO—AATTCATGGCTTATCGACCGTCTGAAACTCTGTGCGGCGGCGAACTG—OH    3'
          ||||||||||||||||||||||||||||||||||||||||||||
3'    HO—GTACCGAATAGCTGGCAGACTTTGAGACACGCCGCCGCTTGACCAAC—³²P 5'
```

Fragments 5, 14, 24, 22, 6 and 4 were annealed and ligated to form Duplex II:

Fragments 7, 8, 9, 25, 26 and 27 were annealed and ligated to form Duplex III:

DNA duplex molecules I, II and III were then mixed and treated with T4 DNA ligase to form a doublestranded molecule with an EcoRI overlap at one end of the molecule and a XbaI overlap at the other end. The ligation product of the reaction involving duplexes I, II and III was purified on a 10% polyacrylamide gel and constitutes about half of the IGFII coding region.

The remainder of the IGFII coding region was synthesized in like manner. Thus, fragments 10, 11 12, 28, 29 and 30 were annealed and ligated to form Duplex IV:

Fragments 23, 13, 15, 16, 31, 32, 33 and 34 were annealed and ligated to form Duplex V:

Fragments 17, 18, 35 and 36 were annealed and ligated to form Duplex VI:

Duplex DNA molecules IV, V and VI were then ligated to form the remaining portion of the IGFII coding region. The ligation produced a DNA molecule with an XbaI overlap at one end and a BamHI overlap at the other. The ligation product was purified on a 10% polyacrylamide gel.

EXAMPLE 4

Construction of Plasmid pIGF201
A. Construction of Plasmid pIGF2

Five μg of plasmid pBR322 are dissolved in 5 μl of TE buffer, and 2 μl 10X BamHI buffer [1.5M NaCl; 60 mM Tris-HCl, pH 7.9; 60 mM MgCl$_2$; and 1 mg/ml bovine serum albumin (BSA)], 1 μl BamHI restriction enzyme (~10 Units) and 12 μl H$_2$O are added, gently mixed and incubated at 37° C. for 2 hours. After the incubation, the BamHI-digested DNA is precipitated and then resuspended in 2 μl 10X EcoRI buffer, 1 μl EcoRI restriction enzyme (~10 Units) and 17 μl H$_2$O. After gentle mixing, the reaction is incubated at 37° C. for 2 hours.

The EcoRI- and BamHI-digested plasmid pBR322 DNA is extracted once with phenol-CHCl$_3$ (50:50), followed by extraction with CHCl$_3$ alone. The DNA is precipitated by making the mixture 0.3M in NaOAc, adding 2.5-3 volumes ethanol, mixing, chilling to −70° C., and centrifuging. The DNA pellet constitutes ~5 μg of the EcoRI- and BamHI-digested plasmid pBR322 DNA. After the DNA is suspended in 25 μl of TE buffer, it is stored at −20° C. for subsequent ligation to the synthetic IGFII-encoding gene fragments.

One μl of the EcoRI- and BamHI-digested plasmid pBR322 is added to 0.6 picomoles each of the EcoRI-XbaI and XbaI-BamHI IGFII-encoding fragments generated in Example 3. The DNA molecules are ligated in substantial accordance with the ligation procedure of Example 3. The ligated DNA is subsequently transformed into E. coli RV308.

B. Construction of Escherichia coli RV308/pIGF2
  1. Preparation of Frozen, Competent Escherichia coli K12 RV308

Five ml portions of TY broth were inoculated with E. coli K12 RV308 (NRRL B-15624), and the resulting culture was incubated at 37° C. overnight with shaking.

The overnight culture was diluted with TY broth to a final volume of 1 liter, resulting in an optical density reading (600 nanometers) of ~0.1 absorbance units. The incubation at 37° C. with shaking was continued until the optical density reading (600 nm) reached the 0.55-0.65 absorbance units range, and then the cells were collected by centrifugation.

The cell pellet was resuspended in 500 ml of chilled 50 mM CaCl$_2$, and the resulting mixture was incubated on ice for 15-30 minutes. The cells were then collected by centrifugation, and the resulting pellet was resuspended in 20 ml of a cold solution of 20% glycerol in 50 mM CaCl$_2$. The cell mixture was then aliquoted in 0.2 ml portions into pre-chilled tubes, which were immediately placed and stored at −70° C. The cells prepared by this procedure remain viable and competent for transformation for up to one year.

2. Transformation

One of the tubes containing the competent E. coli K12 RV308 cells was removed from storage at −70° C., thawed and mixed with the ligated DNA of Example 4A. The cell-DNA mix was incubated on ice for one hour. The cells were then collected, the supernatant discarded, and the pellet resuspended in 0.5 ml of TY broth supplemented with tryptophan at 100 μg/ml. After incubation for 30 minutes at 37° C., the cells were plated on TY plates supplemented with 50 μg/ml ampicillin and 100 μg/ml tryptophan. The plates were incubated at 37° C. overnight.

3. Analysis

The desired transformants were identified by their predicted ampicillin-resistant, tetracycline-sensitive phenotype and by analysis of the plasmid DNA. Since the entire DNA sequence of plasmid pIGF2 can be predicted, the isolated plasmid DNA from the transformed *E. coli* cells is cleaved with different restriction enzymes to determine, by electrophoresis and gel analysis, whether the reaction products are those predicted for pIGF2. The transformants thus identified constitute the desired *E. coli* RV308/pIGF2. Plasmid pIGF2 is prepared and purified in substantial accordance with the teaching of Example 1.

C. Digestion and Dephosphorylation of Plasmid pIGF2

Five μl of plasmid pIGF2, isolated above, were digested with EcoRI in a total volume of 50 μl in substantial accordance with the procedure of Example 4A. The digested plasmid was then extracted with phenol:CHCl₃ (50:50), and precipitated in substantial accordance with the procedure of Example 4A. The EcoRI digested plasmid pIGF2 was then resuspended in 100 μl of phosphatase buffer (10 mM Tris-HCl, pH 8.0; 1 mM MgCl₂; and 0.01 mM ZnCl₂).

This ~4.2 Kb EcoRI digested plasmid pIGF2 suspended in phosphatase buffer was incubated at 65° C. for 5 minutes, and then 1 ml (7 Units Boehringer-Mannheim) of calf-intestinal alkaline phosphatase was added, mixed, and incubation at 65° C. continued for 5 more minutes. The incubation was followed by a 30 minute incubation at 60° C., after which the reaction mixture was extracted once with phenol:CHCl₃ (50:50) and once with CHCl₃. After the extractions, the reaction mixture was made 0.3M in NaOAc; three volumes of ethanol were added; and, after mixing and chilling to −70° C., the solution was centrifuged to pellet the phosphatased fragment. The obtained DNA pellet was suspended in 25 μl of TE buffer and constituted ~4.5 μg of the phosphatased ~4.2 Kb EcoRI digested plasmid pIGF2.

D. Ligation and Transformation

One μl of the dephosphorylated EcoRI-digested plasmid pIGF2 was added to 4 μl of the trpLE1-encoding EcoRI restriction fragment isolated in Example 2 and ligated in substantial accordance with the teaching of Example 4A. The ligated DNA constituted the desired plasmid pIGF201.

The ligated DNA constituting plasmid pIGF201 was used to transfrom *E. coli* K12 RV308 in accordance with the transformation procedure of Example 4B2. The desired transformant,, *E. coli* K12 RV308/pIGF201 was identified by analysis of its plasmid DNA.

EXAMPLE 5

Construction of *Escherichia coli* RV 308/pCZ21

A. Construction of Plasmid pCZ21

1. Isolation of the ~10.1 Kb Eco RI-BamHI vector fragment of pCZ20

Five μg of plasmid pCZ20, from Example 2B, are digested with BamHI and EcoRI restriction endonucleases in substantial accordance with the procedure of Example 4A. The digested plasmid pCZ20 is then electrophoresed on a 1% agarose gel, and the desired ~10.1 Kb EcoRI-BamHI fragment containing the kanamycin resistance gene and the runaway replicon is isolated in substantial accordance to the teaching of Example 2. The DNA pellet is suspended in 25 μl TE buffer and constitutes ~4.0 μg of the ~10.1 Kb EcoRI-BamHI vector fragment of pCZ20.

2. Isolation of the ~0.63 Kb EcoRI-BamHI Restriction Fragment Encoding trpLE1 and IGF-II from Plasmid pIGF201

About 30 μg of plasmid pIG201, from Example 4D, is digested with BamHI in substantial accordance with Example 4A. After precipitation, the DNA is resuspended in 2 μl 10X EcoRI buffer, 1 μl EcoRI restriction enzyme (~10 Units) and 17 μl H₂O. This mixture is gently mixed and incubated at 37° C. After 1 minute, 5 μl of the mixture is removed and mixed with 1 μl 0.25M EDTA to stop the reaction. 5 μl aliquots are likewise removed and mixed with 1 μl 0.25M EDTA after 2, 5 and 10 minutes of incubation. These aliquots are all electrophoresed on a 1.2% agarose gel in substantial accordance with the procedure of Example 2. A small piece of DEAE membrane is placed in front of the desired ~0.63 Kb EcoRI-BamHI fragment, and this DNA is collected and precipitated in substantial accordance with the procedure of Example 2. After the final precipitation, the DNA is resuspended in 20 μl TE buffer and constitutes ~0.35 μg of the desired trp LE1- and IGF-II-encoding EcoRI-BamHI restriction fragment.

3. Ligation

About 1 μl of the ~10.1 Kb EcoRI-BamHI fragment from Example 5A1 is mixed with 4 μl of the ~0.63 Kb EcoRI-BamHI fragment encoding trpLE1 and IGF-II obtained in Example 5A2 and ligated in substantial accordance with the teaching of Example 4A. The ligated DNA constituted the desired plasmid pCZ21.

B. Transformation and Analysis of *Escherichia coli* RV308/pCZ21

1. Transformation

One of the tubes containing the competant *E. coli* K12 RV308 cells was removed from storage at −70° C., thawed and mixed with the ligated DNA of Example 5A3. The cell-DNA mix was incubated on ice for one hour. The cells were then collected, the supernatant discarded and the pellet resuspended in 0.5 ml of TY broth. After incubation for 30 minutes at 25° C., the cells were plated on TY plates supplemented with 50 μg/ml Kanamycin. The plates were inoculated overnight at 25° C.

2. Analysis

Since the entire DNA sequence of plasmid pCZ21 could be predicted, the isolated plasmid DNA from the transformed *E. coli* cells was cleaved with different restriction enzymes to determine, by electrophoresis and gel analysis, whether the reaction products were those predicted for plasmid pCZ21.

EXAMPLE 6

Purification and Characterizaton of Recombinant Human IGF-II

The purification scheme for IGF-II starts with the isolation of granules from heat killed *E. coli* containing the fusion product LE1-Met-IGF-II expressed with the thermoinducible runaway replicon plasmid, pCZ21. The remainder of the purification scheme is similar to that used for purifying the insulin A and B chains and proinsulin expressed in *E. coli*, in that a chimeric protein is cleaved into its component parts and the desired product converted to the S-sulfonate form. The S-sulfonate form is refolded to its native conformation and further purified. The IGF-II purification scheme starts with the fusion product LE1-Met-IGF-II, which contains a shortened version of the trpLE' protein. This chimeric form of IGF-II was used because it produces a large amount of the desired product, by virtue of the small LE1 protein (45 amino acids). The derivatization of the six cysteine residues in IGF-II to S-sulfonates introduced a large number of negative charges enabling the protein to be conveniently purified over an anion exchange column. The LE1 protein contains no cysteine and therefore no S-sulfonate groups after the sulfitolysis reaction. LE1 does not bind to anion exchange columns as it has a net positive charge at pH 7.

Heat killed E. coli cells containing the LE1-Met-IGF-II chimeric protein were suspended in 50 mM Tris-HCl pH 8 (10 ml buffer per gram of wet cell paste) and lysed with lysozyme and $Na_2EDTA$ at final concentrations of 0.4 mg/ml and 5 mM, respectively. The mixture was stirred for 20 minutes at room temperature and then cooled for 20 minutes on ice. The highly viscous suspension was sonicated (3 pulses of 30 seconds each) at 0° C. until the cells were completely lysed. The suspension was centrifuged for 20 minutes at 3000 Xg and 4° C. to separate the cell debris and soluble protein from the granules containing chimeric LE1-Met-IGF-II. The granule pellet was washed successively with 1M NaCl, 1M urea, and, finally, with water. Protein assay and gel electrophoresis were carried out on the granule preparation.

The chimeric protein was cleaved into its component proteins LE1 and IGF-II with cyanogen bromide. The granules were suspended in water (1 ml/10 g original cell paste), and formic acid was added to a final concentration of 75% to dissolve the chimeric protein. The solution was made 2 mM in sodium thiosulfate and 200 mM in cyanogen bromide. Addition of the solid cyanogen bromide was carried out in a hood. The reaction proceeded overnight and the extent of the cleavage was monitored by SDS polyacrylamide gel electrophoresis (PAGE). The reaction mixture was taken to dryness on a rotary evaporator in the hood. The condensate was poured into a bleach solution containing 5.25% sodium hypochlorite (by weight) for disposal. The dry protein film was taken up in the same volume of water and lyophilized.

IGF-II was converted to the S-sulfonate form in 7M urea, 500 mM Tris-base, pH 8.2, with 100 mM sodium sulfite and 10 mM sodium tetrathionate at 5-10 mg/ml of total protein. The pH of the reaction mixture was kept constant with the addition of solid Tris-base.

An analytical Pharmacia Mono Q ™ anion exchange column on an LCC500 FPLC ™ (Fast Protein Liquid Chromatography), system was used to follow the progress of the sulfitolysis reaction and to purify the final S-sulfonate product. The reaction mixture was injected onto the column and washed with 20 mM Tris pH 7.7, in 7M urea. A gradient from 0 to 0.5M NaCl over 20 minutes in 20 mM Tris, pH 7.7, 7M urea was generated by the FPLC ™. Unreacted material eluted with 120 mM NaCl whereas IGF-II $(SSO_3^-)_6$ required 280 mM NaCl. Approximately 80% of the pooled material had a molecular weight of 7500, half of which was judged to be IGF-II $(SSO_3^-)_6$ by SDS PAGE under nonreducing conditions where the S-sulfonate runs with a higher apparent molecular weight. The sulfitolysis reaction mixture was dialyzed against 50 mM ammonium bicarbonate and lyophilized. The resulting impure material was used to generate IGF-II by a procedure similar to that used for proinsulin as described in U.S. Pat. No. 4,430,266. A disulfide interchange reaction was initiated by adding two-fold excess of cysteine over cysteine S-sulfonate groups to 67 μg/ml of IGF-II(SS-$O_3^-)_6$ in 20 mM glycine, pH 10, at 4° C. The reaction was quenched by adding glacial acetic acid until a final concentration of 1M acetic acid was reached. The kinetics were followed by taking an aliquot of the reaction mixture at various time points, quenching the reaction with glacial acetic acid, and measuring the amount of native IGF-II formed. The reaction was complete within ten to sixteen hours.

Native IGF-II was purified by HPLC over a preparative Zorbax ® C-8 150 Å (DuPont) pore column (21.2 mm×25 cm) at room temperature. An acetonitrile gradient comprising an A solvent composed of 0.2M $(NH_4)_2SO_4$, 0.1M $H_2SO_4$, 10% $CH_3CN$ and a B solvent composed of 2M $(NH_4)_2SO_4$, 0.1M $H_2SO_4$, 40% $CH_3CN$ was run at a concentration from 50% to 60% B solvent over one hour at 4 ml/min. The same solvent system and reverse phase packing were used in an analytical column (4.6 mm×25 cm) run isocratically at 40° C. and at 0.5 ml/min with 65% B solvent to detect native IGF-II.

Residual high and low molecular weight impurities were removed during a subsequent solvent exchange over a Bio-Gel ® P-10 (BioRad) column equilibrated in 1M acetic acid. The IGF-II peak from this column was homogeneous by SDS-PAGE, had the correct amino acid composition, and was fully active in the CPBA (Competitive Protein Binding Assay) upon comparison of the binding curve for rat IGF-II with that for human IGF-II using radiolabelled rat IGF-II. Human IGF-II appeared to be slightly more active than rat IGF-II in the CPBA.

EXAMPLE 7

IGF-II Formulation

A typical gel formulation useful for topical administration of IGF-II is composed of the following:

|  | % by Weight |
| --- | --- |
| sterile distilled water | 92.38 |
| sodium dibasic phosphate | 0.03 |
| Carbapol ™ | 0.5 |
| glycerin | 1.6 |
| m-cresol | 0.25 |
| sodium hydroxide (1N) | 0.5 |

To 6 ml of the foregoing is added 3 mg of IGF-II.

EXAMPLE 8

IGF-II Wound Healing Studies

A. The effect of IGF-II on the closure of surgically-induced full-thickness 4 $cm^2$ dermal wounds.

Adult, male, Fischer-344 rats were used as experimental animals. Ether was used as the general anesthesia for all wound placement surgical procedures. Each rat had a single 4 $cm^2$ full-thickness dermal wound placed on its back. The wound was made by cutting the skin with surgical scissors. Following placement of each wound, a telfa-pad bandage was applied to the wound and secured to the rat with adhesive tape. A small hole was cut in the adhesive tape to expose the telfa pad at a spot directly over the wound. To the telfa bandage 0.6 ml of a control solution (0.1M $NH_4H_2PO_4$, pH 7.3) or 0.6 ml of the control solution containing 75 or 150 μg IGF-II per 0.6 ml was applied twice daily for 12 days. The area of the open portion of each wound was measured at days 5, 8, and 12 of the experiment (Table 2). On day 12, all treatment was stopped, and the bandages were removed. On day 15, the area of the scar of each wound was measured (Table 3).

TABLE 2

The effect of IGF-II on area reduction of full-thickness dermal wounds on the backs of rats

| Experimental Group | Mean Area ± S.E.M. (cm²) | | |
|---|---|---|---|
| | Day 5 | Day 8 | Day 12 |
| I. Control | 2.86 ± 0.17 | 1.78 ± 0.10 | 0.65 ± 0.11 |
| II. IGF-II (75 μg) | 2.62 ± 0.15 | 1.63 ± 0.07 | 0.62 ± 0.11 |
| III. IGF-II (150 μg) | 2.23 ± 0.11[a] | 1.29 ± 0.06[a] | 0.31 ± 0.06[a] |

[a]Statistical significance of mean at $P \leq 0.05$ as calculated using Dunnett's test

TABLE 3

The effect of IGF-II on scar area of full-thickness dermal wounds on the backs of rats

| Experimental Group | Mean Scar Area (cm²) |
|---|---|
| I. Control solution | .609 ± .058[a] |
| II. IGF-II (75 μg) | .533 ± .077 |
| III. IGF-II (150 μg) | .472 ± .034 |

[a]Mean ± S.E.M.

The larger dose of IGF-II, applied topically to the wound, significantly reduced the mean wound area as compared to the same parameter measured in the control wounds. By day 15, the open wound areas could no longer be measued and so measurement of the scar area replaced the open wound measurement. The mean scar size of the wounds treated with the higher dose of IGF-II was smaller than the same parameter measured in the control-treated wounds. It is concluded that administration of IGF-II induces more rapid closure of open full-thickness dermal wounds.

B. The effect of IGF-II on the closure of surgically-induced full-thickness 4 cm² dermal wounds.

Adult, male, Fischer-344 rats were used as experimental animals. Ether was used as the general anesthesia for all wound placement surgical procedures. Each rat had a single 4 cm² full-thickness dermal wound placed on its back. The wounds were made by cutting the skin with surgical scissors. Following placement of each wound a telfa pad bandage was applied and secured with adhesive tape. A small hole was cut in the adhesive tape to expose the telfa pad at a spot directly over the wound. To the telfa bandage 0.6 ml of a control solution (0.1M $NH_4H_2PO_4$, pH 7.3) or 0.6 ml of the control solution containing 150 or 300 μg IGF-II per 0.6 ml was applied twice daily for 12 days. The area of the open portion of each wound was measured at days 3, 5, 8, and 12 of the experiment (Table 4). On day 12, all treatment was stopped, and the bandages were removed. On day 15, the area of the scar of each wound was measured (Table 5).

TABLE 4

The effect of IGF-II on area reduction of full-thickness dermal wounds on the backs of rats

| Experimental Group | Mean Area ± S.E.M.[c] (cm²) | | | |
|---|---|---|---|---|
| | Day 3 | Day 5 | Day 8 | Day 12 |
| I. Control | 2.99 ± .17 | 2.00 ± .14 | 1.47 ± .07 | .30 ± .07 |
| II. IGF-II (150 μg) | 2.70 ± .11 | 1.75 ± .09 | 1.10 ± .05[a] | .13 ± .02 |
| III. IGF-II (300 μg) | 2.45 ± .17[a] | 1.61 ± .13[b] | 1.06 ± .08[a] | .12 ± .03 |

[a]Statistical significance of mean at $P \leq 0.05$ as calculated using Dunnett's test
[b]Statistical significance of mean at $P \leq 0.05$ as calculated using Student's T-test
[c]One value greater than 3 times the Standard Deviation for the group was dropped from the calculations.

TABLE 5

The effect of IGF-II on scar area of full-thickness dermal wounds on the backs of rats

| Experimental Group | Mean Scar Area (cm²) |
|---|---|
| I. Control solution | .474 ± .030 |
| II. IGF-II (150 μg) | .255 ± .036 $P \leq .001$[a] |
| III. IGF-II (300 μg) | .339 ± .038 $P \leq .013$[a] |

[a]Statistical significance of mean calculated using Student's T-test.

Both doses of IGF-II, applied topically to the wounds, significantly reduced mean wound area as compared to the same parameter measured in control wounds. By day 15, the open wounds could no longer be measured and so measurement of the scar area replaced the open wound measurement. The mean scar sizes of the wounds treated with both doses of IGF-II were smaller than the same parameter measured in the control-treated wounds. It is concluded that administration of IGF-II induces more rapid closure of open full-thickness dermal wounds.

C. The effect of IGF-II on the closure of surgically induced full-thickness 4 cm² dermal wounds.

Adult, male, Fischer-344 rats were used as experimental animals. Ether was used as the general anesthesia for all wound-placement surgical procedures. Each rat had a single 4 cm² full-thickness dermal wound placed on its back. The wounds were made by cutting the skin with surgical scissors. Following placement of each wound, a telfa-pad bandage was applied to each wound and secured with adhesive tape. A small hole was cut in the adhesive tape to expose the telfa pad at a spot directly over the wound. To the telfa bandage, 0.6 ml of a control solution (0.1M $NH_4H_2PO_4$, pH 7.3) or 0.6 ml of the control solution containing 150 and 300 μg IGF-II per 0.6 ml was applied twice daily for 12 days. The area of the open portion of each wound was measured at days 3, 5, 8, and 12 of the experiment (Table 6). On day 12, all treatment was stopped and the bandages were removed. On day 15, the area of the scar of each wound was measured (Table 7).

TABLE 6

The effect of IGF-II on area reduction of full-thickness dermal wounds on the backs of rats

| Experimental Group | Mean Area ± S.E.M. (cm²) | | | |
|---|---|---|---|---|
| | Day 3 | Day 5 | Day 8 | Day 12 |
| I. Control | 4.04 ± .22 | 2.98 ± .17 | 2.27 ± .15 | .48 ± .04 |
| II. IGF-II (150 μg) | 3.44 ± .14[a] | 2.63 ± .11 | 1.89 ± .08[a] | .34 ± .04[a] |
| III. IGF-II (300 μg) | 3.00 ± .11[a] | 2.41 ± .10[a] | 1.75 ± .09[a] | .33 ± .05[a] |

TABLE 6-continued

| | The effect of IGF-II on area reduction of full-thickness dermal wounds on the backs of rats | | | |
|---|---|---|---|---|
| Experimental | | Mean Area ± S.E.M. (cm$^2$) | | |
| Group | Day 3 | Day 5 | Day 8 | Day 12 |
| μg) | | | | |

$^a$Statistical significance of mean at P ≦ 0.05 as calculated using Dunnett's test

TABLE 7

| The effect of IGF-II on scar area of full-thickness dermal wounds on the backs of rats | |
|---|---|
| Experimental Group | Mean Scar Area (cm$^2$) |
| I. Control solution | .440 ± .033 |
| II. IGF-II (150 μg) | .225 ± .033$^a$ |
| III. IGF-II (300 μg) | .220 ± .029$^a$ |

$^a$Statistical significance of mean calculated using Student's T-test.

Both doses of IGF-II, applied topically to the wounds significantly reduced the mean wound area as compared to the same parameter measured in the control wounds. By day 15, the open wounds could no longer be measured and so measurement of the scar area replaced the open wound measurement. The mean scar sizes of the wounds treated with both doses of IGF-II were smaller than the same parameter measured in the control-treated wounds. It is concluded that administration of IGF-II induces more rapid closure of open full-thickness dermal wounds.

We claim:

1. A pharmaceutical formulation comprising insulin-like growth factor-II (IGF-II) and a pharmaceutically acceptable carrier suitable for topical administration.

2. Formulation of claim 1, in which the carrier is an ointment.

3. Formulation of claim 1, in which the carrier is a cream.

4. Formulation of claim 1, in which the carrier is a gel.

5. Formulation of claim 1, in which the IGF-II is present in an amount sufficient to afford from about 1 to about 500 μg per cm$^2$ of wound.

6. Formulation of claim 5, in which the IGF-II is present in an amount sufficient to afford from about 30 to about 300 μg per cm$^2$ of wound.

7. Formulation of claim 6, in which the IGF-II is present in an amount sufficient to afford from about 50 to about 200 μg per cm$^2$ of wound.

8. Formulation of claim 7, in which the IGF-II is present in an amount sufficient to afford from about 60 to about 100 μg per cm$^2$ of wound.

9. A method for promoting the rate and improving the quality of wound healing, which comprises topically applying to such wound insulin-like growth factor-II (IGF-II) in an amount sufficient to reduce the normal healing time.

10. Method of claim 9, in which the amount of insulin-like growth factor-II is administered in a range which does not produce a systemic insulin-like effect.

11. Method of claim 9, in which the IGF-II is applied in an amount sufficient to afford from about 1 to about 500 μg per cm$^2$ *of wound*.

12. Method of claim 11, in which the IGF-II is applied in an amount sufficient to afford from about 30 to about 300 μg per cm$^2$ of wound.

13. Method of claim 12, in which the IGF-II is applied in an amount sufficient to afford from about 50 to about 200 μg per cm$^2$ of wound.

14. Method of claim 13, in which the IGF-II is applied in an amount sufficient to afford from about 60 to about 100 μg per cm$^2$ of wound.

* * * * *